(12) United States Patent
Roschin et al.

(10) Patent No.: US 8,987,338 B2
(45) Date of Patent: *Mar. 24, 2015

(54) ACTIVE INGREDIENT OF A MEDICINAL AGENT, A MEDICINAL AGENT, A PHARMACEUTICAL COMPOSITION AND METHOD FOR TREATING DEMENTIA SYNDROME PATIENTS

(76) Inventors: Viktor Ivanovich Roschin, St. Petersburg (RU); Vagif Sultanovich Sultanov, St. Petersburg (RU)

( * ) Notice: Subject to any disclaimer, the term of this patent is extended or adjusted under 35 U.S.C. 154(b) by 531 days.

This patent is subject to a terminal disclaimer.

(21) Appl. No.: 12/601,377

(22) PCT Filed: May 14, 2008

(86) PCT No.: PCT/RU2008/000297
§ 371 (c)(1),
(2), (4) Date: Feb. 22, 2010

(87) PCT Pub. No.: WO2008/143551
PCT Pub. Date: Nov. 27, 2008

(65) Prior Publication Data
US 2010/0178327 A1    Jul. 15, 2010

(30) Foreign Application Priority Data
May 23, 2007 (RU) ............................. 2007119232

(51) Int. Cl.
A61K 9/127 (2006.01)
A61K 31/045 (2006.01)
A61K 9/28 (2006.01)
A61P 25/28 (2006.01)
C07C 33/03 (2006.01)
A61K 31/745 (2006.01)

(52) U.S. Cl.
CPC .................................... A61K 31/745 (2013.01)
USPC .......... 514/739; 424/450; 424/474; 568/909.5

(58) Field of Classification Search
None
See application file for complete search history.

(56) References Cited

FOREIGN PATENT DOCUMENTS

| GB | 2310138 A | * | 8/1997 |
| RU | 2137479 C1 | | 9/1999 |
| RU | 2252026 C1 | | 5/2005 |

OTHER PUBLICATIONS

Moore, A.H., O'Banion, M.K., Neuroinflammation and anti-inflammatory therapy for Alzheimer's disease. Adv. Drug Del. Rev. 54 (2002) 1627-2656.*

Solagran Annual Report, 2004.*
Solagran Company Announcement, Sep. 20, 2005 (provided by applicant in PTO-1449 dated Nov. 2, 2009).*
Imrich Blasko and Beatrix Grubeck-Loebenstein. Role of the Immune System in the Pathogenesis, Prevention and Treatment of Alzheimer's Disease. Drugs Aging 2003; 20 (2): 101-113.*
Solagran Limited, "Company Announcement Final Results of Bioeffective R Alzheimer's Disease Trail", Sep. 20, 2005, pp. 1-5, Found on the Internet URL:hhttp://wrww.osullivanpllc.com/news/050920solagran.pdf.
European Office Action corresponding to European Patent Application No. EP 08779161.2, dated Aug. 29, 2011.

* cited by examiner

*Primary Examiner* — Frederick Krass
*Assistant Examiner* — Michael P Cohen
(74) *Attorney, Agent, or Firm* — Foley & Lardner LLP

(57) ABSTRACT

The invention relates to an area of the chemical-pharmaceutical industry and medicine, particularly to an agent for treatment of dementias, including Alzheimer's disease (AD), as well as to a method of treatment and pharmaceutical composition, which is effective for both treatment of dementias, including AD or dementias of Alzheimer type, and during manifestations of the first symptoms of memory disorder.

The given invention consists of the development of a new therapeutic substance with minimal side effects that currently is a topical issue for treatment of the corresponding diseases. Attached is the use of polyprenols of formula (1)

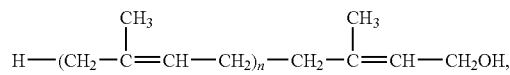

where n=8-20
as an active ingredient for the production of the therapeutic agent for the treatment of patients with dementia syndrome, including those who suffer from Alzheimer's disease.
It is proposed to use a therapeutic agent for the treatment of patients with dementia syndrome, including those suffering from Alzheimer's disease, being polyprenols of formula (1). It was proposed that a pharmaceutical composition for the treatment of patients suffering from dementia syndrome, including patients suffering from Alzheimer disease, being an effective amount of polyprenols of formula (1) and pharmaceutically acceptable additional substances, including carriers and/or solvents, additives and/or lubricants.
It was proposed that a method for treatment of patients suffering from dementia syndrome, including patients suffering from Alzheimer's disease, when effective amount of polyprenols of formula (1) is administered in the form of the substance or as a pharmaceutical composition that includes additional components.

10 Claims, No Drawings

ACTIVE INGREDIENT OF A MEDICINAL AGENT, A MEDICINAL AGENT, A PHARMACEUTICAL COMPOSITION AND METHOD FOR TREATING DEMENTIA SYNDROME PATIENTS

TECHNOLOGICAL FIELD

The invention relates to an area of the chemical-pharmaceutical industry and medicine, particularly to an agent for treatment of dementias, including Alzheimer's disease (AD), as well as to a method of treatment and pharmaceutical composition, which is effective for both treatment of dementias, including AD or dementias of Alzheimer type, and during manifestations of the first symptoms of memory disorder.

LEVEL OF TECHNOLOGICAL INVENTION

In Western countries, AD presents as senile dementia in middle-aged people and in the elderly. According to data from the National Institute of Gerontology, 4.5 millions Americans suffer from this disease and it annually costs the economy 100 billion dollars. AD might turn into a serious problem as the world's population is living longer.

AD leads to gradual degeneration of the neurons of the brain. The molecular and cellular mechanisms of neuronal damage and loss are not yet fully understood. AD is classified as a mitochondrial disease and belongs to a class of complex multifactorial diseases. In these types of diseases there is mitochondrial dysfunction caused by mutations of mitochondrial and nuclear DNA. In the initial stages the mechanism leading to loss of neurons is overstimulation of glutamate receptors. This is followed by an influx of calcium to cells, which disrupts the function of cellular mitochondria and the uptake of energy reserves. In people suffering from AD, cholinergic and dopaminergic reserves are exhausted. AD is characterised by brain cognitive dysfunction, reduced memory and intelligence, as well as by expressed behavioural pathology. Research in the area of AD is taking place around the world and there are a number of hypotheses to explain the start of this disease.

However, in all cases the start and development of AD is associated with the presence of toxic β-amyloid, a change in membrane structure and in its lipid layer. Current research shows that an increase in the secretion level of β-amyloid peptide, which causes toxic activity in the body and induces oxidative stress in the tissues and the organs, plays a role in AD pathogenesis. Therefore, this peptide is regarded as a target for the development of new approaches for effective therapy such as the use of β- and γ-secretase inhibitors. The level of β-amyloid is primarily defined by the activity of membrane-bound secretase that breaks down the amyloid protein precursor (APP). Changing the activity of these secretases is regarded as one method of AD therapy. The condition and structure of both the endoplasmic reticulum and lysosomal membranes, which contain the corresponding secretases, are important for normal functioning of these enzymes. Using specifically synthesised test-substances for the treatment of AD, research was carried out to determine the action and condition of the brain microsome membranes and the membranes of hepatic lysosomes and on membrane viscosity In brain microsomes, a significant increase in micro-viscosity of the lipid bio-layer was seen, whereas in the lysosomes, the ratio of phospholipids in the membrane's bio-layer changed and the micro-viscosity in the erythrocytes increased. According to the AD literature, increased micro-viscosity occurs adjacent to the proteins contained in lipid membranes. There is also an increase in lipid peroxidation (LP) level. In other words, disruption in one of the major system of metabolism regulation, such as lipid peroxidation homeostasis system is directly related to membrane functioning.

Substances which affect the function and condition of membranes and regulate the system of LP homeostasis were considered promising as therapeutic agents for the treatment of AD.

The toxic effect of β-amyloid is also the induced by oxidative stress. One of the products of oxidative stress is hydrogen peroxide and the oxidative degradation of lipids that occurs in the lipid peroxidation reaction. As well as formation of amyloid plaques, the onset of AD is related not only with aging, but also with such pathological brain conditions such as acute and chronic hypoxia, ischemia, and stroke.

The new class of molecular chaperones, the polytopic membrane proteins (PS1 and PS2), control access and indirectly have an effect on the activity of proteases in the transmembrane domain of APP and play a role in the development of AD. Proteases of similar properties are involved in the proteolytic activation of the transcriptional factor for regulation of cholesterol biosynthesis in the membranes. The trigger for the development of various types of dementias and AD is atherosclerosis of the vessels in the brain which can lead to the formation of senile plaques in the cerebral cortex. Data is available showing a correlation between AD, and Down's syndrome and gene mutations in these diseases. Hence, substances (such as statins and nicotinic acid) that are involved in the biosynthesis or regulation of cholesterol and the impaired lipid blood spectrum can be used as therapeutic agents for the prophylaxis and treatment of AD.

There is a significant change in acetylcholinesterase inhibitor (AChE) activity in patients with AD. This results in a decrease in the level and duration of action of the neurotransmitter acetylcholine (ACh) in the brain, and is one of the causes of memory loss. The choice of a therapeutic agent in AD is determined by a loss of cortical cholinergic. In Russia Physostigmine and Amiridine are used for the treatment of AD and other dementias. In other countries, Tacrine, Donepizil, and inhibitors of AChE (Halantamine and Rivastigmine (U.S. Pat. No. 5,409,948)), and Phenserine (application WO03/082270) are the treatments of choice. NMDA-receptor antagonists, such as Memantine and Dimebon (patent RU 2106864), are also used for treatment of AD.

It is assumed that in addition to AChE, regulation of acetylcholine levels in the brain are also controlled by butyrylcholinesterase (BuChE), which has also been found in senile plaques, fibrillar glomerules and in the vessel walls (in amyloid angiopathy). Patients with AD have a decreased level of cholinergic transmission, a reduction in AChE activity and an increase in BuChE activity. Both AChE and BuChE, are localised in amyloid plaques and have the capacity to increase the aggregation of the amyloid peptide. It has been shown that AChE inhibitors, not only block the activity of acetylcholine, but can also inhibit the formation of the amyloid peptide. When AChE contributes to the transmission of nerve impulses, then BuChE is not present in neurotransmission. The role of BuChE is not fully understood in neurotransmission. In blood serum, BuChE is synthesised in the endoplasmic reticulum of the liver parenchymal cells therefore, the level of BuChE activity is one of the indicators of the functioning of the liver. Experimental and clinical data demonstrate that inhibition of BuChE leads to an improvement in the learning abilities, memory and visual-spatial functions. Therefore, it is more favourable to use double-action therapeutic agents, that is, inhibitors of both AChE and BuChE, for the treatment of AD. Rivastigmine has double-action properties and the use of this drug causes a positive effect on patients after only 12 weeks of therapy. However, this drug is very expensive and treatment involves prolonged use of this agent. As well as a deficit in cholinergic transmission, a deficit of adrenergic neurons (which also contributes to memory loss and behavioural disorders) has been found in AD patients. This especially occurs at the early stages of the disease. In recent times, the roles of dopamine blocking drugs in the treatment of AD and related dementias have been discussed.

The deficit of adrenergic impulses directly correlates with the development and expression of depression in patients with AD. There is also 3-fold increase in the activity of monoamine oxidase (MAO), another very important enzyme. Increased MAO activity also affects the development of amyloid plaques. Based on these observations, research for double-action substances (that is, inhibitors of AChE and MAO) that can be used for the treatment of AD, has been conducted around the world (Veselovsky A. V. Biomedical chemistry 2004 Vol. 50 Ed. 3, p. 314-321).

Cholinesterase inhibitors that correct the acetylcholine deficit in the hippocampus of the brain is the common course of therapy used in the treatment of AD. The choice of a therapeutic substance is determined by the pathogenetic mechanism of the disease, namely, the loss of cholinergic. Cholinesterase inhibitors have a weak, but evident effect on improvement of cognitive functions and temper other symptoms of the disease. However, the effect of these therapeutic agents has a temporary effect and does not lead to restoration of cholinergic. Moreover, these therapeutic agents have a wide range of side effects, among which the most common are nausea, vomiting, diarrhoea and dizziness. The disadvantages of using these drugs include prolonged treatment, the high cost of the therapy and side effects. Therefore, the dilemma is how to find new, effective and inexpensive therapeutic agents that have minimal side effects.

The closest analogue to our invention is Gliatilin, a therapeutic agent based on choline alfoscerate which contains 40.5% of choline). Gliatilin, a cholinotropic agent, serves as a donor for the biosynthesis of ACh in the presynaptic membranes of the cholinergic neurons. It is effective as a therapy for progressive dementia and chronic deficiency of blood circulation in the brain and associated memory loss. In addition, it is effective as a treatment for locomotive disorders, brain encephalopathy and congenital degenerative diseases of the central nervous system (application EP1203584). However, the positive effects of Gliatilin therapy were seen mainly in patients with brain-vascular deficiency (patent RU 2217143) and alcohol encephalopathy. Improvements in cognitive functions were seen only in patients with mild or moderate level of dementia. An effect was not seen in cases of moderate to severe dementia, (Odinak M. M., Voznyuk I. A. New approaches in therapy of acute or chronic pathology of nervous system, Study material, SPb, HMA, 2001, p. 62).

THE INVENTION

The objectives of this invention include development of a new agent and a treatment of AD that does not have the disadvantages outlined in the previous sections. In addition, we are searching for new therapeutic agents that have minimal side effects. Currently, these are topical issues in the treatment of different neurodegenerative diseases.

The targeted issues have been resolved as follows.

It is proposed that we will use polyprenols of formula (1)

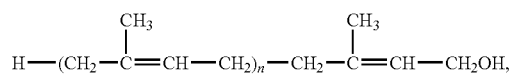

where n=8-20
as an active ingredient for the production of a therapeutic agent for the treatment of patients with dementia.

It is proposed that we will use polyprenols of formula (1)

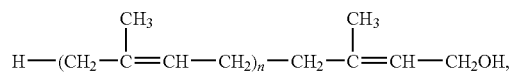

where n=8-20
as an active ingredient for production of a therapeutic agent for the treatment of patients with Alzheimer's disease.

It is proposed that we will use an agent for the treatment of patients with dementia, including those suffering from Alzheimer's disease. This will be a polyprenol with the following formula (1)

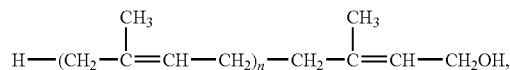

where n=8-20.

The pharmaceutical composition for the treatment of patients with dementia, including those suffering from Alzheimer's disease, will include efficacious amounts of polyprenols of formula (1)

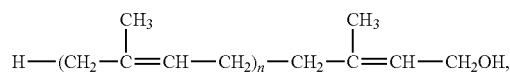

where n=8-20
and pharmaceutically acceptable excipients, including carriers, and/or solvents, additives, and/or lubricants. The pharmaceutical composition can be produced in the following forms: solution, suspension, coated tablet, tablet, capsule, rectal suppository, or liposomal form. The pharmaceutical composition can be an oil solution, a suspension for parenteral administration, or a solid or liquid form for oral administration, with the content of polyprenols ranging from 0.10 to 80% by weight.

It is proposed a method for the treatment of patients with dementia, including those suffering from Alzheimer's disease, will receive efficacious amount of polyprenols of formula (1)

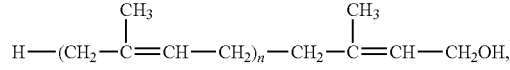

where n=8-20
as an individual agent or in a form of a pharmaceutical composition including excipients.

The authors of the invention identified a previously unknown option to treat patients with dementia and cognitive function disorders, including those Alzheimer's disease, using polyprenols of formula (1)

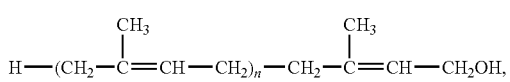

where n=8-20.

Polyprenols of formula (1) are a natural mixture of oligomers (isoprenols) that act as an integral substance obtained from green needles of coniferous species (patent RU 2017782). This polyprenol has demonstrated anti-ulcer activity (N. A. Skuya and others). Products of the processing of green verdure have a potential use in gastroenterology (Functional diagnostics and efficacy of treatment of diseases of digestive tract Vilnuis 1988 part 4 p. 675-676), hepatoprotector (U.S. Pat. No. 5,731,357).

It is preferable to obtain a more pure fraction of isoprenols, Ropren, using a method, described in patent RU2238291.

This method is based on the extraction of green conifer needles and foliage of deciduous species using an organic solvent. Following removal of coniferous wax by settling and filtration after cooling, separation of free acids from the solution of extractive compounds in the hydrocarbon solvent is carried out using alkali solution.

Fractionation of the neutralised solution of salts in the solution of neutral compounds is carried out with a hydrocarbon solvent and a water-alkaline solution of salts and organic acids. The neutral substances are subsequently extracted by acetone and $C_1$-$C_3$ alcohol, using a 1:2 to 1:5 "neutral substances to extractant" % w/w ratio. During extraction with acetone, neutral substances separate into a fraction containing higher fatty acid esters, triterpene alcohol, stearins, and higher fatty alcohols—and an acetone-soluble fraction. Upon treatment of the acetone soluble fraction with alcohol, the total diterpene alcohols are separated from the alcohol insoluble, polyprenol acetates. Saponification of the latter with alcoholic alkali solution results in a polyprenol concentrate. These polyprenols, with a density of 0.893-0.897 g/ml, were obtained by chromatography of a given concentration of substance using a silica gel, with the ratio of substance:sorbent of 1:10 in hexane, or in hexane with addition of 5% and 10% of diethyl ether, with sorbent-solvent ratio of 1:1. The HPLC chromatogram should contain peaks with a shape and location typical for a chromatogram of polyprenols of formula (1). Chromatography set-up: 3.0×150 mm column filled with octadecyl silica gel of X-Terra $C_{18}$ type or similar; mobile phase—acetone-methanol mixture (80:20); flow rate—1 ml/min.

The basis for use of the compound of formula (1) for the claimed means was identification of a series of new activities, which were previously unknown for this compound.

It was found that polyprenols of formula (1) are double-action inhibitors of such enzymes as MAO and BuChE that enabled the assumption of their efficacy for treatment of patients with dementia-type neurodegenerative diseases accompanied by cognitive brain function disorder, including patients with Alzheimer's disease.

EXAMPLES OF PROFFERED EXECUTION OF THE INVENTION

The authors of this invention studied and researched the activity of polyprenols of formula (1) in the mentioned patient groups, its effect on parameters of MAO and BuChE activity during the course of treatment, with the results of this work presented below.

Activity of MAO and BuChE in the blood plasma was determined in 15 patients with vascular dementia of Alzheimer's type and with Parkinson's syndrome. Activity of MAO was determined spectrophotometrically (at 241 nm) based on the amount of benzaldehyde, which forms as a result of enzymatic reaction of oxidative desamination of monoamines in the blood plasma (Zeinalov T. A., Gorkin V. Z. Issues of medical chemistry, 1990, 36 (1): 78-81). The blood was sampled from a vein and using this method, activity of MAO in the blood plasma was determined before and after treatment with Ropren.

Normal value of MAO activity in healthy individuals (blood donors) is on average 0.44 nmol per 1 ml of plasma per 1 min. MAO activity in the examined patients varied depending on their age and conditions from 0.57-1.26 nmol per 1 ml of plasma per 1 min before treatment (except for 3 patients—0.19-0.28 nmol per 1 ml of plasma per 1 min). After completion of treatment with isoprenols of formula (1), MAO activity decreased by between 0.47 to 0.91 nmol per 1 ml of plasma per 1 min*.

Comparison of the results of the blood test of each patient before and after the treatment showed the following: MAO activity of blood plasma in the patients was higher than the standard, before the treatment in 1.3-2.9 times and only in 3 patients it was lower than standard and remained without any changes after the treatment (data obtained from the patients was not included for referencing range of parameters of MAO activity after the treatment).

As a result of the treatment, MAO activity decreased in almost all patients to normal or close to normal values (i.e. by 1.5-3 times).

Therefore, it was demonstrated that the compound of formula (1) has an inhibiting activity on MAO activity of the blood plasma.

Activity of BuChE was determined as per Ellman's method (Ellman G. L., Coutney K. D. et al. Biochem. Pharmacol. 1961 7 (1): 88-95; Kolb V. V., Kalashnikov V. S. Clinical biochemistry. Guidelines for medical laboratory assistants, Minsk, 1976, p. 109).

Before the test, blood plasma of the patients was defrosted and diluted with water by 10-30 times and subject to BuChE activity. BuChE activity was determined by this method before and after the treatment with Ropren. BuChE activity in 15 patients varied depending on their age and conditions from 0.98 to 1.79 nmol per 1 ml of plasma per 1 min before the treatment (except for 3 patients—2.7-3.1 nmol per 1 ml of plasma per 1 min). 2 months after the treatment, activity of BuChE decreased to between 0.09 to 0.19 nmol per 1 ml of plasma per 1 min in all patients. After completion of the treatment with polyprenols of formula (1), activity of BuChE remained at low levels of between 0.15 to 0.53 nmol per 1 ml of plasma per 1 min or increased slightly (in 3 patients with exceptionally high initial level—1.28-1.58 nmol per 1 ml of plasma per 1 min). The inhibiting effect of Ropren on BuChE activity was reversible in some patients. However, it was demonstrated that during administration of the test-substance for a period of 3 months BuChE activity decreased on average by 3-20 times.

Administration of polyprenols of formula (1) to the patients can be as the polyprenols "as is", or as a part of pharmaceutical composition in combination with pharmaceutically acceptable carriers, solvents and excipients.

Examples of pharmaceutical compositions include any solid (such as tablets, pills, capsules, granules, etc.) or liquid (such as solutions, suspensions, emulsions), therapeutic forms for internal administration, traditional forms for parenteral administration, or in a form of rectal suppositories.

Compositions for oral administration can contain traditional excipients. They can be prepared in solid or liquid forms such as tablets, capsules, solutions, suspensions or syrups. They can contain any acceptable excipients such as binding agents (eg sugar, gelatine, sorbitol, tragacanth, polyvinylpyrrolidone), fillers (lactose, sugar, starch, calcium phosphate, sorbitol), lubricants (eg magnesium stearate), disintegrants (eg starch, polyvinylpyrrolidone, microcrystalline cellulose, carboxymethylcellulose), wetting agents (eg sodium lauryl sulphate), and dispersing surfactants. Liquid forms for oral administration can include solvents (such as water, vegetable or animal oils, or mineral oil), dextrose and other solutions of saccharides, glycols. The above-mentioned compositions are prepared using traditional and conventional methods. These methods include mixing of the active ingredients with a carrier, and can include one or more excipients, and a finished product mixture is obtained from the mixture.

Tablets can be obtained by compression, using special equipment. In this case, an active ingredient, in a form of powder or granules is mixed, if necessary, with binding agents (eg povidone, gelatin, hydroxypropylmethylcellulose), lubricants, inert solvents, disintegrants (such as cellulose derivatives, cross-linked povidone, sodium carboxymethyl cellulose), surfactants or dispersing agents. Tablets are obtained by moulding using the appropriate equipment, and contain a mixture of wetted powder compound of formula (1) with inert liquid solvents. If necessary, tablets can be coated for slow or controlled release of the active ingredient. Coatings for the tablets can be obtained using excipients such as hydroxypropylmethylcellulose or its mixture with gelling agents (gelatine, waxes) at different ratios, to obtain the preferred releasing profile.

Composition for parenteral administration can be prepared by both traditional pharmaceutical methods (such as solutions, suspensions), and in a form of water micro-emulsions as per patent RU 2189231 based on Hanks solution with 10% of ethanol. They can include water, pharmaceutically acceptable fats or oils, alcohols or other organic solvents, surfactants and/or antioxidants. Normal concentrations of the compound of formula (1) are within the range from 0.10 to 80%.

Finished compositions can contain a single dose or be produced in a form of ampoules or vials, which contain several single doses. If necessary, finished therapeutic forms can contain stabilizers, buffer systems, and other excipients.

Agents for rectal administration can include traditional substances, such as paraffin, vegetable, animal or mineral fats or oils, emulsifiers, polyethylene glycol, lauryl sulphate or sulphate salts, mineral acids or sodium hydrogen carbonate.

Examples of the pharmaceutical compositions are presented below.

Liquid Peroral Form

| It contains the following components | |
|---|---|
| | (weight %) |
| The compound of formula (1) | 10.0-60.0 |
| Sunflower oil | remainder to 100.0 |

Below are examples 1 and 2 of possible compositions for the liquid therapeutic form of the substance.

Example 1

| | |
|---|---|
| The compound of formula (1) | 25.0 |
| Sodium ascorbate | 0.1 |
| Vitamin $B_6 + B_{12}$ | 0.1 |
| Sunflower oil | remainder. |

Example 2

| | |
|---|---|
| The compound of formula (1) | 25.0 |
| Essential phospholipids | 25.0 |
| Sunflower oil | remainder. |

The compound of formula (1) and sunflower oil are mixed together, and with any other excipients present, in the above-mentioned proportions, then the mixture is dispensed into vials using a suitable doser and sterilised.

Example 3

| Suspension for parenteral administration. It contains the following components | |
|---|---|
| | (weight %) |
| The compound of formula (1) | 20 |
| Tween 80 | 25.0 |
| Ethanol | 4.0 |
| Polypropylene glycol | 10.0 |
| Pyrogen-free water | remainder. |

The compound of formula (1) is mixed with ethanol and polypropylene glycol, and Tween 80, and then heated. Water is added and the solution is stirred thoroughly. The mixture is dispensed into ampoules and sterilised.

Example 4

| Gelatin capsules. Capsules contain the following components | |
|---|---|
| | (weight %) |
| The compound of formula (1) | 46.0 |
| Copolymer of methacrylic acid | 12.0 |
| Talc | 5.7 |
| Copolymer of methacrylic and acrylic acids | 18.0 |
| Glycerol triacetate | 3.3 |
| Magnesium stearate | 15.0 |

Example 5

| Gelatin capsules. | |
|---|---|
| Weight of the capsules | 238-262 mg (100%) |
| The compound of formula (1) | 20.0 weight % of capsule's weight |

Example 6

| Gelatin capsules. | |
|---|---|
| Weight of the capsules | 240-260 mg (100%) |
| The compound of formula (1) | 6.0 weight % of capsule's weight |
| Sunflower oil | 14.0 weight % of capsule's weight |

Example 7

| Gelatin capsules. | |
|---|---|
| Weight of the capsules | 240-260 mg (100%) |
| The compound of formula (1) | 4.0 weight % of capsule's weight |
| Sunflower oil | 16.0 weight % of capsule's weight |

Example 8

| Gelatin capsules. | |
|---|---|
| Weight of the capsules | 412-420 mg (100%) |
| The compound of formula (1) | 48.0 ± 0.5 weight % of capsule's weight |

Example 9

| Gelatin capsules. | |
|---|---|
| Weight of the capsules | 412-420 mg (100%) |
| The compound of formula (1) | 2.4 ± 0.1 weight % of capsule's weight |
| Sunflower oil | 47.0 ± 0.2 weight % of capsule's weight |
| Sodium ascorbate | 0.1 weight % of capsule's weight |
| Vitamin $B_6 + B_{12}$ | 0.1 weight % of capsule's weight |

Example 10

| Gelatin capsules. | |
|---|---|
| Weight of the capsules | 412-420 mg (100%) |
| The compound of formula (1) | 10.0 ± 0.2 weight % of capsule's weight |
| Sodium ascorbate | 0.1 weight % of capsule's weight |
| Vitamin $B_6 + B_{12}$ | 0.1 weight % of capsule's weight |

Example 11

| Gelatin capsules. | |
|---|---|
| Weight of the capsules | 208-212 mg (100%) |
| The compound of formula (1) | 24.0 ± 0.2 weight % of capsule's weight |

Example 12

| Gelatin capsules. | |
|---|---|
| Weight of the capsules | 208-212 mg (100%) |
| The compound of formula (1) | 5.0 ± 0.1 weight % of capsule's weight |
| Sunflower oil | 19.0 ± 0.2 weight % of capsule's weight |

Capsules that are mentioned in examples 4-12 do not contain components of animal origin. The compound of formula (1) is mixed with vegetable oils or in a mixture with oil and the other components, in the above proportions, and then placed into an apparatus to obtain the therapeutic form. Then, the capsules are dried to 3-5% water content at a temperature not exceeding 45° C.

Example 13

| Soft gelatine capsules. | |
|---|---|
| The compound of formula (1) | 10.0 weight % |
| Vegetable oil | 50.0 weight % |
| Capsule coating | 40.0 weight % |

The compound of formula (1) is mixed with vegetable oil (soy, olive, sunflower, corn, etc.) and placed in soft capsules, made of carrageen, glycerine, hydroxypropyl starch, dibasic sodium phosphate, then packed into vials or in blister packs, and sterilised if appropriate.

Example 14

| Liquid-liposomal form of the substance. The agent contains the following components | |
|---|---|
| | (weight %) |
| Compound of formula (1) | 0.4 |
| Lecithin | 4.0 |
| Preservative | 0.001-0.2 |
| Water | remainder. |

The liposomal form is prepared using the method of mechanical emulsification in liquid phase from soy-bean lecithin, which is then subjected to additional purification. The compound of formula (1) was added to a composition of lipids in chloroform solution with further evaporation and with the subsequent addition of water and emulsification.

The effective amount, as per the claimed use, is within the range from 1 to 200 mg and can be administered in a form of a single, or of several doses per day. More specific doses depend on the type of pathology, patient's condition, presence of accompanying diseases. The selection of doses and duration of treatment depend strictly on the individual and their condition.

The efficacy of the treatment of Alzheimer-type dementias with marked intellectual-mnestic memory loss with polyprenols of formula (1) and a comparison of the efficacy of Ropren and Gliatilin was studied in patients during a 3-month course of treatment. Treatment efficacy on various functions before and after the treatment was assessed using the international scale MMSE ((evaluation of mental status—Mini-Mental State Examination, MMSE) Folstcin et al, 1975), "list with symptoms" questionnaire, unified scale for evaluation of Parkinsonism, EEG data, and biochemical parameters of the blood.

Clinical trials of the substance were conducted at the St. Petersburg Skvortsova-Stepanova Municipal Psychiatric Hospital No. 3 in patients with Alzheimer's type dementia caused by vascular damage of the brain.

Patients diagnosed with vascular dementia of the Alzheimer's type can be divided into 4 groups using MMSE scale, age and severity of disease: 1. patients with a mild form of dementia (12%), 2. patients with a moderately expressed form (36%), 3. patients with a moderately severe form (32%), and 4. patients with severe form—20% (Table 1). The Duration of the treatment with Ropren was, on average, 3 months, and 8 patients received the medication for 4 months. These patients suffered from the severe form of dementia. Many patients had a medical history of Parkinson's syndrome.

Clinical trials of the product were conducted in Russia at St. Petersburg's municipal institutions: "St Georgiy Hospital", Botkin's hospital No. 30, 1 and 2 therapeutic units of the clinics of Medical Academy Postgraduate Education, Centre for prophylactics and treatment of AIDs and infectious diseases. These trials revealed that the product is safe and effective.

The characteristics of the patients are presented in Table 1. Polyprenols of formula (1) were prescribed at the dose of 20-200 mg per day, whereas Gliatilin (choline alfoscerate) was prescribed at a dose of 400 mg, twice per day.

TABLE 1

Characteristics of patients before and after Ropren treatment

| Parameter | Before treatment | After treatment |
|---|---|---|
| Age (years) | 66, 76 | Same |
| Men:Women | 14:11 | Same |
| Duration of disorder | From 3 months to 4 years | Same |
| Evaluation of severity of dementia as per MMSE scale | | |
| Very mild (% of patients) | None | 12 |
| Mild (% of patients) | 12 | 32 |
| Moderate (% of patients) | 36 | 20 |
| Moderately severe (% of patients) | 32 | 24 |
| Severe (% of patients) | 20 | 12 |

By the $2^{nd}$ month of Ropren treatment, there was a marked improvement in the general condition of the patients, with disappearance of anxiety, complaints of depressive type symptoms, hypochondriacal complaints, tearfulness, more rational behaviour was exhibited by the patients. Half of the patients noted the disappearance of headaches, dizziness and loss of coordination while walking. Irritability and tendency to affective behaviour decreased.

MMSE scale (parameter of evaluation of intellectually-mnestic functions of a patient before and after treatment) was used for the evaluation of intellect. Improvement of cognitive functions was found in 22 patients (88%) who received Ropren for at least 3 months. Electroencephalography (EEG) was performed in 12 patients (48%) before and after the Ropren therapy. EEG results help in differential diagnosis of the disease.

During the process of aging and dementia, the frequency of the main EEG rhythms is unusually retarded. These changes are the most marked in the frequency spectrum within the range of alpha-rhythms. The frequency of these waves falls in healthy people over 60 years old, and in cases of pathology, they can disappear altogether, or have non-synchronous and irregular rhythms (the so-called "timing mechanism of the brain"). Currently, analysis of EEG parameters is used to identify the biological age of the brain. Mental health significantly depends on the precision of this timing mechanism. Changes in nervous activity of the brain is an indicator of the long-term vitality of the body, when after a course of treatment with the substance, EEGs increase in rhythm frequency, or in some patients, not only are alpha-rhythm frequencies restored, but they also re-emerge. As a rule, evaluation of the mental state of such patients using the MMSE scale was higher by 11 points after treatment with polyprenols.

In general, EEG analysis revealed positive changes in most patients, according to data obtained by both visual examination and analysis of power spectra that comprise bioelectric activity (BEA). There was a distinct shift in spectral density towards a high-frequency range and δ-rhythm, an increase in its activity, and a decrease in the emphasis in the left fronto-temporal lobe. Delta-waves and paroxysms disappeared. This indicates the optimisation of the functional condition of cortical neurons, expressed through their activation in the patients after Ropren therapy (75%). After Ropren therapy, there were no changes in 2 patients (16.6%), whereas negative changes were found in 1 patient. EEG data revealed that positive changes after Ropren therapy was found in patients at the early stages of the disease. No changes in EEG results were found after the Gliatilin treatment.

Investigation of neurological status revealed that administration of Ropren for 3 months has a moderate therapeutic effect in Parkinson's syndrome. After treatment with Ropren, the Parkinson's syndrome decreased (on average by 5 points) in almost all patients, i.e., in 23 out of 25 patients or in 92%. This positive effect was found as early as 1 month after commencement of Ropren therapy. In the case of Gliatilin, improvement of Parkinson's syndrome was less pronounced (on average by 3 points) using the Parkinsonism rating scale. Also, Gliatilin was less effective in reducing the symptoms in cases of the vascular type dementias.

Therefore, polyprenols of formula (1) can be used as an agent to treat patients with dementia syndrome and those with a diagnosis of the Alzheimer's-type dementia, for both mild and moderate-severe forms of the disease.

The following changes were found in patients with the moderately severe form of the disease: reduction of the number of complaints related to vegetovascular disorders, improvement in general condition, increase in vitality and a reduction in the severity of the dementia. In some patients with AD, the severe form of dementia transformed into the moderate-severe form.

The effect of the substance on cognitive functions depended on the duration of the clinical dementia. Improvement of cognitive functions such as memory, intellect and attention was assessed as 5-7 points better (on average) using the MMSE scale. Mostly, the improvement was related to such functions as active attention, long-term memory, orientation in space, and improvement of speech. The observed improvement in functioning was noted by both the patients themselves, and by doctors and other medical staff.

The most pronounced therapeutic effect of the treatment with polyprenols of formula (1) was observed in the patients with the combined pathology: cranio-cerebral trauma and alcoholism with background of vascular dementia. Improvement of parameters of mental status (as per MMSE scale), improvement in biochemical parameters and positive changes in EEG were found.

In all patients, treatment with polyprenols of formula (1) resulted in an improvement of general condition, a decrease in the number of anxious-depressive and hypochondriac complaints, normalisation of biochemical parameters of the blood and improvement of CNS activity based on EEG and MMSE data. However, changes in neurological status were less evident, than after treatment with Gliatilin.

TABLE 2

Comparative parameters of the blood, EEG, and mental status of the patients before and after Ropren treatment

| Card No. *P | Before treatment with Ropren / After treatment with Ropren | Biochemical blood indices | | | | | | Evaluation of mental status Points | EEG data Changes in EEG |
|---|---|---|---|---|---|---|---|---|---|
| | | Cholesterol | AP | ALT | Sugar | Bilirubin | Thymol test | | |
| 1. 3 months | Before treatment | 6.21 | 168.4 | 37.2 | 4.27 | 16.21 | 0.2 | 0 | – |
| | After treatment | 6.27 | 169.4 | 36.4 | 4.28 | 15.41 | 0.3 | 5 | – |
| 2. 1 year | Before treatment | 7.27 | 184.1 | 38.3 | 5.81 | 16.27 | 0.32 | 20 | Without |
| | After treatment | 6.17 | 168.6 | 37.1 | 5.71 | 15.49 | 0.27 | 21 | peculiarities |
| 3. 1 year | Before treatment | 6.21 | 176.3 | 37.4 | 5.81 | 18.26 | 0.4 | 16 | – |
| | After treatment | 6.71 | 139.7 | 37.2 | 5.18 | 15.27 | 0.3 | 18 | – |
| 4. 1 year | Before treatment | 6.69 | 176.5 | 40.2 | 4.87 | 15.49 | 0.3 | 20 | – |
| | After treatment | 6.01 | 162.7 | 38.4 | 4.27 | 15.21 | 0.27 | 24 | – |
| 5. 1.5 year | Before treatment | 4.69 | 179.4 | 38.9 | 5.23 | 15.54 | 0.3 | 24 | Negative |
| | After treatment | 4.67 | 171.2 | 37.9 | 5.21 | 15.26 | 0.27 | 26 | |
| 6. 2 months | Before treatment | 6.21 | 170.4 | 37.9 | 4.28 | 15.27 | 0.3 | 26 | – |
| | After treatment | 6.27 | 168.4 | 36.8 | 4.29 | 15.81 | 0.3 | 26 | – |
| 7. 6 months | Before treatment | 4.89 | 170.3 | 36.9 | 5.21 | 15.54 | 0.3 | 24 | – |
| | After treatment | 4.87 | 169.7 | 37.2 | 5.37 | 15.25 | 0.3 | 28 | – |
| 8. 6 months | Before treatment | 4.78 | 170.4 | 42.1 | 6.21 | 18.31 | 0.4 | 21 | + |
| | After treatment | 4.86 | 169.8 | 41.4 | 5.59 | 16.82 | 0.3 | 27 | |
| 9. 1 year | Before treatment | 4.72 | 169.4 | 47.2 | 6.81 | 19.27 | 0.5 | 7 | – |
| | After treatment | 4.81 | 167.8 | 42.4 | 6.87 | 18.27 | 0.4 | 14 | – |
| 10. 3 years | Before treatment | 6.82 | 169.7 | 36.4 | 6.07 | 17.25 | 0.4 | 3 | Positive |
| | After treatment | 6.27 | 168.9 | 37.4 | 5.59 | 15.71 | 0.3 | 7 | |
| 11. 3 years | Before treatment | 6.28 | 181.4 | 44.1 | 6.28 | 15.27 | 0.3 | 2 | – |
| | After treatment | 6.24 | 169.8 | 41.4 | 6.01 | 15.07 | 0.2 | 7 | – |
| 12. 1 year | Before treatment | 6.84 | 179.4 | 27.4 | 4.81 | 13.27 | 0.2 | 10 | – |
| | After treatment | 6.28 | 169.1 | 28.2 | 4.37 | 13.84 | 0.21 | 16 | – |
| 13. 1 year | Before treatment | 6.81 | 174.2 | 36.8 | 7.01 | 18.21 | 0.8 | 9 | – |
| | After treatment | 6.71 | 167.1 | 34.8 | 6.01 | 18.27 | 0.4 | 13 | – |
| 14. 1 year 6 months | Before treatment | 6.01 | 171.0 | 21.6 | 6.01 | 15.01 | 0.2 | 16 | Positive |
| | After treatment | 5.91 | 174.1 | 26.7 | 5.27 | 15.54 | 0.3 | 19 | α-rhythm |
| 15. 4 years | Before treatment | 4.87 | 145.2 | 16.8 | 4.41 | 16.10 | 0.1 | 20 | No |
| | After treatment | 5.71 | 160.2 | 221.7 | 4.82 | 15.25 | 0.3 | 20 | changes |
| 16. 1 year 6 months | Before treatment | 7.27 | 181.0 | 37.2 | 6.01 | 20.71 | 1.2 | 10 | – |
| | After treatment | 6.78 | 176.4 | 37.6 | 5.81 | 17.04 | 0.3 | 15 | – |
| 17. 1 year | Before treatment | 6.01 | 169.1 | 32.7 | 4.27 | 15.27 | 0.3 | 16 | Positive |
| | After treatment | 5.89 | 168.7 | 37.1 | 4.08 | 15.07 | 0.2 | 20 | norm |
| 18. 1 year | Before treatment | 4.78 | 161.0 | 37.1 | 4.89 | 15.01 | 0.1 | 12 | Without |
| | After treatment | 4.89 | 159.8 | 37.4 | 4.81 | 15.54 | 0.3 | 17 | changes |
| 19. 1 year | Before treatment | 8.01 | 169.7 | 40.1 | 5.81 | 18.04 | 0.4 | 5 | – |
| | After treatment | 7.79 | 167.4 | 37.8 | 5.71 | 18.04 | 0.4 | 10 | – |
| 20. 1 year | Before treatment | 6.81 | 161.0 | 31.6 | 4.71 | 17.01 | 0.4 | 10 | – |
| | After treatment | 6.74 | 178.1 | 31.6 | 5.01 | 15.56 | 0.3 | 14 | – |
| 21. 1 year | Before treatment | 7.01 | 161.8 | 34.8 | 4.87 | 15.91 | 0.3 | 14 | Positive |
| | After treatment | 6.68 | 161.3 | 40.4 | 5.11 | 17.61 | 0.4 | 27 | α-rhythm |
| 22. 6 months | Before treatment | 5.01 | 174.1 | 121.4 | 7.01 | 24.01 | 1.2 | 21 | Positive |
| | After treatment | 5.71 | 168.1 | 37.2 | 6.41 | 15.61 | 0.3 | 28 | To norm |
| 23. 6 months | Before treatment | 4.85 | 151.4 | 74.2 | 7.01 | 21.04 | 1.0 | 15 | Positive |
| | After treatment | 6.71 | 151.4 | 27.9 | 5.79 | 15.57 | 0.3 | 26 | |
| 24. 1 year | Before treatment | 5.71 | 161.4 | 97.6 | 7.07 | 41.2 | 2.0 | 10 | Positive |
| | After treatment | 5.97 | 164.2 | 37.1 | 5.84 | 15.79 | 0.4 | 26 | α-rhythm |
| 25. 1 year | Before treatment | 6.07 | 148.4 | 71.0 | 5.81 | 21.04 | 1.4 | 18 | Positive |
| | After treatment | 5.79 | 168.2 | 37.1 | 5.41 | 15.71 | 0.4 | 29 | α-rhythm |

Note:
*P—patients, history of disorder - from 3 months to 3 years.

In 10 patients (or 40%) treated with Ropren there was almost complete reduction of all symptoms, a good orientation in space, and clear improvement of the cognitive functions. In 12 patients (48%), there were less pronounced, but still positive changes of psychosomatic status, which were evident through improvement of orientation in space, adaptation, and self-service skills. However, in 3 (12%) of patients treated with Ropren for more then 3 months, there was no improvement in cognitive function. These patients were older than 70 and had suffered from the disorder for more than 1.5 years. These patients remained disorientated in space, though they became less confused, less affectively charged, more placid, and more manageable in terms of their behaviour. In spite of the symptoms of amnestic disorientation, these patients became better adapted and their self-service skills improved.

Examples of the effect of Ropren on the patients are presented below.

The best clinical results were obtained after treatment of the patients with the mixed-type dementia (vascular+traumatic+toxic) with a history of the disease ranging from 6 months to 3 year. After treatment with Ropren, biochemical parameters of the blood normalised, EEG data showed positive changes, and evaluation of mental status in the patients after treatment, exceeded 11 points.

Example 1 Patient L., 66 years old, the Alzheimer's type vascular brain disorder, chronic alcoholism, history of the disease—6 months. Form of dementia—moderate. Evaluation of the mental status improved from 21 to 28 points as per the scale. Biochemical parameters before and after the treatment: cholesterol—5.01/5.71; AP—174.1/168.1; ALT—121.4/37.2; sugar—7.01/6.41; bilirubin—24.1/15.61; thymol test—1.2/0.3. EEG data taken before and after the treatment indicated positive changes (EEG was normal after treatment). Based on the unified scale of evaluation of Parkinson's disease, there was a 2-point improvement found after the Ropren therapy (35 before and 33 after the treatment).

Example 2 Patient A., 56 y.o., diagnosis: organic brain disorder, cranio-cerebral trauma, vascular dementia with memory loss, alcoholism. History of the disease—6 months. Form of dementia—moderate. Evaluation of the mental status improved from 15 to 26 points after treatment with Ropren. Based on the unified scale of evaluation of the Parkinson's disease, a 5-point improvement was found after Ropren therapy (39 before and 34 after the treatment). Biochemical parameters of the blood: cholesterol—4.85/6.71; AP—157/151.4; ALT—74.2/27.9 Sugar—7.01/5.79, bilirubin—21.04/15.57; thymol sample—1.0/0.3. EEG data: positive changes; appearance of alpha-rhythms.

Example 3 Patient K. 73 y.o., diagnosis—vascular disease of the brain of the Alzheimer's-type with memory loss. Form of dementia—moderate. Evaluation of mental status showed a 10 to 26-point improvement. Biochemical parameters of the blood: cholesterol—5.71/5.77; AP—161/164.2; ALT—97.6/37.1 Sugar—7.01/5.84, Bilirubin—41.2/15.79, thymol test—2.0/0.4. EEG data: positive changes. There was a clear shift in spectral density towards a high-frequency range and 6-rhythm, increase of its activity, and decrease of the emphasis in the left frontotemporal lobe. Delta-waves and paroxysms disappeared. Based on the unified scale of evaluation of the Parkinson's disease, there was a 6-point improvement after Ropren therapy (56 before and 50 after the treatment).

Example 4 Patient C., 54 y.o., diagnosis: organic brain disorder with memory loss, cranio-cerebral trauma, vascular dementia. Form of dementia—moderate-severe. History of the disease—1 year. Evaluation showed mental status improved from 18 to 29 points; biochemical blood indices improved significantly. Biochemical parameters of the blood: cholesterol 6.07/–5.79; AP—148/168; ALT 71.0/37.1. Sugar 5.81/5.72; bilirubin—21.04/15.71; thymol test—1.4/0.4, positive changes in EEG data, appearance of alpha-rhythms, after the treatment EEG returned to norm. Based on the unified scale of evaluation of Parkinson's disease, there was a 5-point improvement found after the Ropren therapy (47 before and 42 after the treatment).

Example 5 Patient I., 60 y.o., disease: organic disease of the brain with a memory loss. Diagnosis: Vascular dementia of Alzheimer's type, dementia syndrome, change of personality. Patient with deep amnestic disorientation, unaware of her age, family status, or family members. Form of dementia—severe. History of the disease—3 year. Evaluation of the mental status before/after treatment was 3/7. Biochemical parameters of the blood: cholesterol—6.82/6.27, AP—169.7/168.9, ALT—36.4/37.4, sugar—6.07/5.59, bilirubin—17.25/15.71, thymol test—0.4/0.3. Positive change in EEG, disappearance of delta-waves and paroxysms, amplification of alpha-rhythm. Self-service skills appeared.

The examples demonstrate that improvement of the patients' condition after 3 months of therapy with Ropren was observed in CNS functioning, and also in metabolism of the main organs and biochemical parameters of the blood.

Therefore, polyprenols of formula (1) can be used as an agent for treatment of patients with dementia syndrome and diagnosed with dementia of the Alzheimer's type in both the mild and moderate-severe forms of the disease. The following changes were found in patients with the moderately severe form of the disease: reduced number of complaints related to vegetovascular disorders, improvement of the general condition, increase of vitality and reduction in the severity of dementia. In some of the patients with AD, the severe form of dementia transformed into moderate-severe form.

It is established that the initiation of AD begins with atherosclerosis of brain vessels, which can be accompanied by the formation of senile plaques in the cerebral cortex. This leads to the development of various types of dementias, for instance, during senile atherosclerosis and related memory disorders.

It is also known, that the age-related decrease in levels of antioxidants, together with metabolic and immunological dysfunction is the facilitating, if not the determining, factor in many age-related memory disorders, including in the development of AD. Before being diagnosed with AD, many patients suffered from gradual decline in memory and ability to concentrate, which is called moderate cognitive disorder (MCD). Not all patients develop AD as a result of this, however, the percentage of transformation of one state into another is reasonably high, around 33%.

Randomised, double blind, placebo controlled trials of Ropren were conducted on patients with marked age-related disorder of memory function and signs of depression. Healthy volunteers (100 people, aged 60-80 y.o.) received Ropren at the dose of 50 mg per day (a 2.5-fold lower dose, than during treatment of patients with AD) for 12 weeks under supervision of Professor Con Stough (Professor of Cognitive Neurology) at the Swinburne Neuropsychologycal Centre (Swinburne University of Technology, Melbourne, Australia).

Participants of this experiment were divided into two groups and went through a number of cognitive and psychomotor tests before administration of the test-substance and placebo, after 2 weeks, and at the end of the treatment (after 12 weeks). All participants went through a strict selection process (as per experiment's selection criteria), which excluded an intake of substances effecting memory and psychoemotional conditions during the experiment, such as tranquilizers, cerebroprotectors, neuroleptics, antidepressants, and even substances of natural origin (i.e. *Ginkgo biloba* extracts). Moreover, all participants were recommended to exercise a special dietary regime. Biochemical parameters and the lipid spectrum of the blood were observed in all participants. Cognitive activity was evaluated using a set of tests developed at the Swinburne University for evaluation of cognitive abilities (Pipingas & Stough, 2003), which were specifically developed for elderly patients, and adequately reflect age-specific cognitive changes. Cognitive tests were conducted in 5 stages: 1st stage—evaluation of attention consistency, 2nd stage—evaluation of short-memory and working memory (test AVLT), 3rd stage—evaluation of long term-memory or episodic secondary memory, 4th stage—motor function control (ability to coordinate and control movements), and 5th stage—evaluation of psychomotor function of the brain, attention and high level of processing of digital data and aspects of working memory. The experiment included such standard questionnaires as Profile of Mood States (as per POMS scale), evaluation of Beck Depression and Anxiety Inventories (BDI, BDA scales), Depression and Anxiety Scale (DAS), Occupational Stress Inventory-revised (OSI-R). Statistical analysis and data processing was conducted using the dispersion method of analysis (ANOVA) across two time segments. Changes of EEG were analysed in 37 participants from the placebo group and experimental groups.

As a result of the experiment, it was established that by the end of 12 weeks of treatment, the group of participants who received Ropren had an increase of 30% in long-term and short-term memory capacity and attention level, when compared with the control group who received placebo. A significant increase in the recovery rate of long-term memory was observed after a 12-week course of Ropren administration. This means faster processing of information and access to systems of long-term memory. The rate of information processing in the frontal part of the brain was faster in those taking Ropren, compared with those taking a placebo. A particularly significant difference was observed between the groups in relation to the parameters of Ray Auditory Verbal Learning Test (Ray AVLT), when process of verbal comprehension and consolidation of verbal material in long-term memory improved due to the Ropren therapy, whereas in the placebo group these functions sharply declined over the same period of time. EEG data revealed that Ropren modified the bioelectric potential of the brain, with particularly effective changes in the frontal parts of the brain, responsible for a complex of cognitive functions, that confirms the acceleration of neural processes during working memory tasks.

As a result of the treatment with Ropren, the total cholesterol level in the blood significantly decreased, as well as the level of low density lipoproteins (LDLP) (by 30%), and the LDLP/HDLP ratio. Out of all types of lipids, LDLP is primarily affected by lipid peroxidation. Lipid peroxidation processes in LDLP particles makes them highly atherogenic leading to changes in the brain's vessels, formation of atherosclerotic plaques, thus increasing the risk of the development of heart attack and dementia.

INDUSTRIAL APPLICABILITY

Therefore, medication based on polyprenols of formula (1) inhibits the activity of enzymes, which participate as neuromediators in cholinergic transmission of neurons, providing a positive effect during treatment of patients with dementia syndrome, for instance, patients diagnosed with Alzheimer's-type dementia.

Based on the presented information, it can be concluded that in comparison to its competitors utilisation of polyprenols of formula (1) (therapeutic substance Ropren) for treatment of Alzheimer's-type dementia has a number of advantages, such as efficacy, safety, a mechanism of double action, and the availability of raw material obtained from by-products of the forest industry.

This therapeutic substance can help patients with the first signs of memory disorder. Due to the absence of side effects, treatment with polyprenols of formula (1) can continue for extended period of time.

The invention claimed is:

1. A method of treating dementia syndrome in a human patient in need thereof, said method comprising administering a therapeutically effective amount of a composition comprising a polyprenol of formula (I)

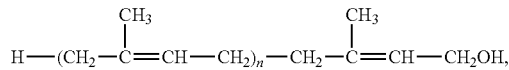

where n=8-20,
wherein said therapeutically effective amount provides a dose of said polyprenol of 20-200 mg per day.

2. The method according to claim 1 wherein said dementia syndrome is Alzheimer's disease.

3. The method according to claim 1 wherein said composition further comprises one or more pharmaceutically acceptable excipients, carriers, solvents, additives, and/or lubricants.

4. The method according to claim 3 wherein said composition is prepared in the form of a solution, suspension, coated tablet, tablet, capsule, rectal suppository, or in liposomal form.

5. The method according to claim 4 wherein said composition is an oil solution, a suspension for parenteral administration, or a solid form for oral administration, and wherein the polyprenol constitutes from 0.10 to 80 weight % of the composition.

6. The method according to claim 1 wherein the method is effected over a period of time of at least 3 months.

7. The method according to claim 6 wherein the method results in improved mental status.

8. The method according to claim 6 wherein the method results in a lower severity of dementia as reflected in a Mini-Mental State Examination scale score.

9. The method according to claim 6 wherein the method results in a reemergence of or improvement in EEG alpha-rhythms.

10. The method according to claim 6 wherein the method results in a reduction in one or more biochemical blood indices selected from the group consisting of cholesterol, alkaline phosphatase (AP), alanine-amino transferase (ALT), sugar, bilirubin and thymol test.

* * * * *